(12) United States Patent
Leinsing et al.

(10) Patent No.: US 6,802,490 B2
(45) Date of Patent: Oct. 12, 2004

(54) NEEDLE FREE MEDICAL CONNECTOR WITH EXPANDED VALVE MECHANISM AND METHOD OF FLUID FLOW CONTROL

(75) Inventors: Karl R. Leinsing, Raleigh, NC (US); Theodore J. Mosler, Raleigh, NC (US)

(73) Assignee: Alaris Medical Systems, Inc., San Diego, CA (US)

(*) Notice: Subject to any disclaimer, the term of this patent is extended or adjusted under 35 U.S.C. 154(b) by 106 days.

(21) Appl. No.: 09/998,383

(22) Filed: Nov. 29, 2001

(65) Prior Publication Data

US 2003/0098430 A1 May 29, 2003

(51) Int. Cl.[7] ............................................. F16K 51/00
(52) U.S. Cl. .................... 251/149.6; 604/249; 604/905
(58) Field of Search ........................ 251/149.1, 149.6; 604/249, 256, 905

(56) References Cited

U.S. PATENT DOCUMENTS

| | | | |
|---|---|---|---|
| 4,749,003 A | 6/1988 | Leason | |
| 5,122,123 A | 6/1992 | Vaillancourt | |
| 5,203,775 A | 4/1993 | Frank et al. | |
| 5,242,432 A | 9/1993 | DeFrank | |
| 5,353,837 A | 10/1994 | Faust | |
| 5,360,413 A | 11/1994 | Leason et al. | |
| 5,439,451 A | 8/1995 | Collinson et al. | |
| 5,509,433 A | 4/1996 | Paradis | |
| 5,616,129 A | 4/1997 | Mayer | |
| 5,616,130 A | 4/1997 | Mayer | |
| 5,676,346 A | 10/1997 | Leinsing | |
| 5,685,866 A | 11/1997 | Lopez | |
| 5,699,821 A | 12/1997 | Paradis | |
| 5,820,601 A | 10/1998 | Mayer | |
| 5,836,923 A | 11/1998 | Mayer | |
| 5,839,715 A * | 11/1998 | Leinsing | ............ 251/149.1 |
| 6,029,946 A | 2/2000 | Doyle | |
| 6,048,335 A | 4/2000 | Mayer | |
| 6,050,978 A * | 4/2000 | Orr et al. | ............ 604/249 |
| 6,063,062 A | 5/2000 | Paradis | |
| 6,152,900 A | 11/2000 | Mayer | |
| 6,183,448 B1 | 2/2001 | Mayer | |
| 6,245,048 B1 | 6/2001 | Fangrow, Jr. et al. | |
| 6,428,520 B1 * | 8/2002 | Lopez et al. | ............ 604/249 |

FOREIGN PATENT DOCUMENTS

| | | |
|---|---|---|
| WO | WO 98/26835 | 6/1998 |
| WO | WO 98-50106 | 11/1998 |

* cited by examiner

Primary Examiner—Eric Keasel
(74) Attorney, Agent, or Firm—Fulwider Patton Lee & Utecht, LLP

(57) ABSTRACT

A needle free medical connector includes a housing with a first port and a second port. The connector also includes a piston element defining a fluid passageway between the first and second ports. The piston element is movable between flow and non-flow positions. The piston element has a compressible section having a variable inner width that forms a part of the flow path through the connector. As the piston is compressed to the flow position, the compressible section self-expands in width thereby maintaining or increasing the volume of the fluid passageway through the connector. The compressible section has a configuration permitting the continuous flow of fluid through its entirety.

23 Claims, 10 Drawing Sheets

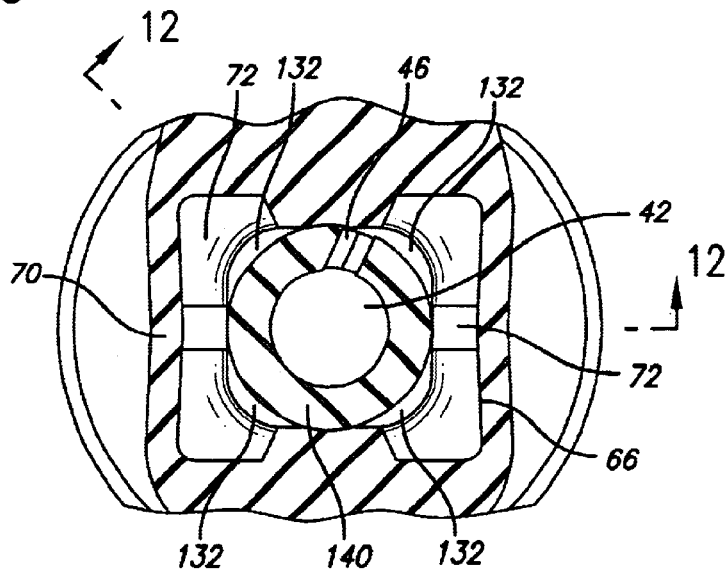
FIG. 13
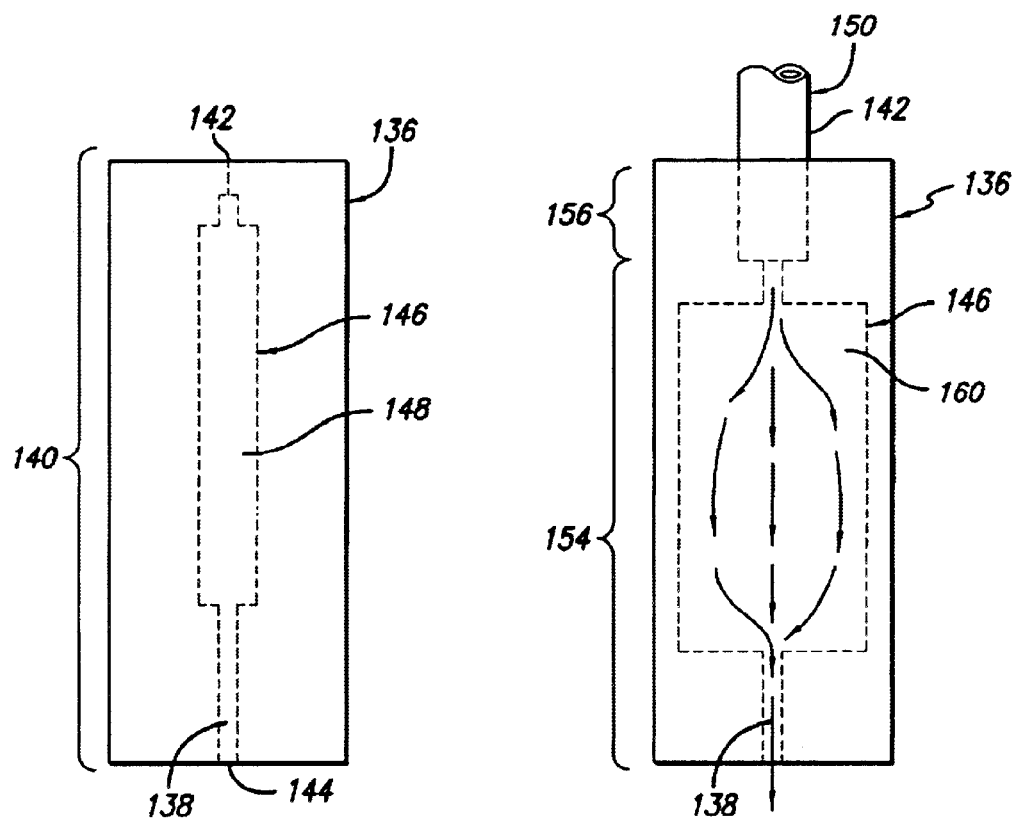
FIG. 14
FIG. 15

NEEDLE FREE MEDICAL CONNECTOR WITH EXPANDED VALVE MECHANISM AND METHOD OF FLUID FLOW CONTROL

INCORPORATION BY REFERENCE

We hereby incorporate by reference U.S. Pat. No. 5,676,346 to Leinsing.

BACKGROUND

The invention relates generally to medical connectors of the type used in the handling and administration of parenteral fluids, and more particularly, to a needle free connector employing a valve mechanism that compensates for negative fluid displacement, i.e., drawing fluid into the connector, as the connector returns to its unaccessed state from an accessed state.

Within this specification the terms, "negative-bolus effect," "positive-bolus effect," and "no-bolus effect" are used to describe the operating characteristics of medical connectors as the connector returns to its unaccessed state from an accessed state. "Negative-bolus" effect describes the condition during which fluid is drawn into the connector as the connector returns to its unaccessed state from an accessed state. "Positive-bolus effect" describes the condition during which fluid is expelled out of the connector as the connector returns to its unaccessed state from an accessed state. "No-bolus effect" describes the condition during which fluid displacement is neutralized and fluid is neither drawn into nor expelled out of the connector as the connector returns to its unaccessed state from an accessed state.

Needle free medical connectors for injecting fluid into or removing fluid from an intravenous ("IV") fluid administration set are well known and widely used. One conventional type of such a connector includes a housing having connection ports at both ends. One connection port may comprise a female Luer port sized to receive a blunt male cannula, such as a male Luer taper. The other connection port may be located opposite the first port but in some cases is located at a ninety degree or other angle to the first port, and comprises a male Luer fitting. In many cases the second port of the connector is permanently connected to IV tubing which in turn is connected to an IV catheter that communicates with a patient's venous system.

A valve is located within the connector and in most cases uses the housing of the connector as part of the valve mechanism. When the connector is accessed, the valve opens an internal fluid passageway between the first and second ports. In some connectors, the internal fluid passageway is defined by the internal boundaries of the connector housing; in other connectors it is defined by an internal cannula or hollow spike; and still in others, the internal fluid passageway is defined by a compressible tubular body that carries the valve mechanism.

Many needle free medical connectors create fluid displacement as the connector is accessed and unaccessed. As the connector is accessed by a blunt male Luer cannula tip inserted into the inlet or first port of the connector housing, the valve mechanism is engaged. In some connectors, the blunt cannula tip penetrates a valve device to establish fluid communication with the internal fluid flow path of the connector. In other connectors, the blunt cannula tip displaces a valve device without penetrating it in order to establish fluid communication with the fluid flow path. In either case, the volumetric capacity of the fluid flow path is often reduced by the insertion of the blunt cannula when accessing the connector. Subsequently, when the blunt cannula is removed from the connector, the volumetric capacity of the fluid flow path increases. This increase in the volumetric capacity may create a partial vacuum or pressure reduction in the fluid flow path that may draw fluid into the connector from the second or downstream end of the connector. As previously mentioned, the effect of drawing fluid into the connector in this manner is referred to as a "negative-bolus" effect in that a quantity, or "bolus," of fluid is drawn into the partial vacuum or reduced pressure location within the connector.

A negative-bolus effect as the connector returns to its unaccessed state is undesirable to some medical care providers and either a neutral bolus or positive bolus effect is preferred. It is therefore desirable to arrange for a valve mechanism that either does not affect the capacity of the internal fluid passageway through the connector as the connector is returned to its unaccessed state, or that actually decreases it.

In one approach, the negative-bolus effect may be reduced or eliminated by clamping the IV tubing between the connector and the IV catheter prior to removal of the blunt cannula from the connector. This prevents the back flow of fluid through the IV catheter and into the connector. However this is an undesirable approach in that another device, i.e. a clamp, is necessary and the care provider must remember to engage the clamp with the tubing. Furthermore, the use of additional devices adds expense and causes inconvenience in that they may not be available at the time needed. Additional steps are also undesirable in that most care providers are very busy already and would therefore naturally prefer to reduce the number of steps in providing effective care to patients rather than increase the number.

In another approach, one that disadvantageously also increases the number of steps in the administration of medical fluids, the operator continually injects fluid into the connector from the male device while the male device is being disengaged from the connector. By continuously adding fluid the operator attempts to fill the increasing fluid volume of the fluid flow path through the connector as the male Luer is being withdrawn, thereby reducing the likelihood of a partial vacuum and thus the likelihood of a negative bolus forming in the fluid flow path. However, this approach is also undesirable in that not only does it add a step but may require some skill in successfully carrying out the procedure.

The negative-bolus effect may also be reduced by the design of the medical connector. As previously mentioned, some medical connectors include an internal cannula or hollow spike housed inside the connector body. The internal cannula or spike is positioned to force open a septum upon depression of the septum onto the internal cannula or spike by a blunt cannula. The internal cannula or spike has an orifice at the top and, upon depression of the septum over the internal cannula or spike, the internal cannula or spike is put directly into fluid communication with the blunt cannula. The internal cannula or spike provides a generally fixed-volume fluid-flow path through the connector. Thus, as the septum returns to its closed position the partial vacuum formed within the connector, if any, is not as large as the partial vacuum formed in a connector having a more volumetrically variable internal fluid passageway. A disadvantage of typical connectors having an internal cannula or spike is a lower fluid-flow rate caused by the small lumen in the cannula or spike. Additionally, it has been noted that with the connector design having a fixedly-mounted internal spike and a movable septum that is pierced by that spike to permit fluid flow, such pierced septum may be damaged with multiple uses and a leaking connector may result.

Another connector provides a valve mechanism that includes a flexible body within which is located a relatively rigid leaf spring. The housing of the connector includes an internal cannula and upon depression of the flexible body by the introduction of a blunt cannula through a port, the internal cannula forces the leaves of the leaf spring apart. The leaves in turn force the top of the flexible body apart and open a slit contained therein. The opening of the slit establishes fluid communication between the accessing blunt cannula and the lumen of the internal cannula. The expanding leaf spring also creates a reservoir-type area between the flexible body and the outer wall of the internal cannula in which fluid is held. As the external blunt cannula is removed from the connector, the leaf spring and reservoir collapse and fluid is forced out of the reservoir and into the internal cannula lumen.

This positive displacement of fluid may result in a positive bolus effect as the valve returns to its unaccessed state. However, the valve mechanism is relatively complex with a leaf spring being incorporated into a flexible member which adds some manufacturing concerns as well as at least one additional part; i.e., the leaf spring. Manufacturing concerns and additional parts can tend to cause expenses to rise, an undesirable effect in the health care industry today where manufacturers strive to provide effective products at lower costs. Further, the reservoir-type system does not permit continuous flow through the entire expandable flexible body section. Instead, fluid flows into the reservoir and is retained there until the valve is returned to its unaccessed state.

Hence, those concerned with the development of medical connectors have recognized the need for a medical connector having a valve mechanism that avoids the negative-bolus effect by producing either a positive-bolus effect or a no-bolus effect. The need for a medical connector that provides these effects without sacrificing fluid-flow rate or structural simplicity has also been recognized. Further needs have also been recognized such as the need for a medical connector that is less expensive to manufacture, that is efficient in operation, and that includes fewer parts. The present invention addresses such needs and others.

SUMMARY OF THE INVENTION

Briefly, and in general terms, the invention is directed to a medical connector having a valve mechanism that provides either a positive-bolus effect or a no-bolus effect, upon deactuation of the valve mechanism. A connector is provided for controlling the flow of fluid, the connector having an internal fluid passageway by which fluid may flow through the connector, the connector comprises a housing having a first port and a second port, the first port being adapted to receive a blunt cannula and the second port adapted for fluid communication with a fluid conduit, and a movable element positioned within the housing, the movable element having a first position at which the movable element blocks fluid flow through the housing and a second position at which the movable element permits fluid flow through the housing, the movable element comprising a head defining a bore forming a part of the fluid passageway through the connector, the head being configured such that when the movable element is in the second position, the bore self-opens to permit fluid flow, the head being further configured such that when the moveable element is in the first position the bore moves to a closed configuration preventing fluid flow, and a compressible section defining an inner conduit forming a part of the fluid passageway through the connector, the inner conduit having a width moveable between a first width and a second width, the compressible section being configured so that when the moveable element is in the second position the compressible section self-expands so that the inner conduit has the second width, the inner conduit being further configured so that when the moveable element is in the first position the inner conduit moves to the first width, wherein the first width is smaller than the second width.

In more detailed aspects, the first and second widths of the inner conduit of the compressible section are selected such that the fluid passageway has a first volume when the movable element is in the first position and a second volume when the movable element is in the second position, the second volume being larger than the first volume. Further, the first and second widths of the inner conduit of the compressible section are selected such that the fluid passageway has a first volume when the movable element is in the first position and a second volume when the movable element is in the second position, the second volume being approximately the same as the first volume. Also, the inner conduit of the compressible section is configured such that fluid may continuously flow through the entire inner conduit when the movable element is located in the second position.

In other more detailed aspects, the connector further comprises a support tube having opposing ends, the support tube defining a lumen extending between the opposing ends, one end being in fluid communication with the second port and the lumen forming a part of the internal fluid passageway through the connector. The support tube comprises a wall, the wall defining a slot providing a fluid path between the exterior of the tube and the lumen. The support tube is configured in relation to the moveable element such that, when the movable element is in the second position, the lumen and slot of the support tube are positioned, at least in part, within the inner conduit of the compressible section such that fluid may flow through the inner conduit of the compressible section, through the slot, through the lumen of the support tube, and through the second port of the housing.

In yet other more detailed aspects, the inner conduit of the compressible section has opposing first and second ends, the first end being adjacent the bore of the head, and the movable element defines an orifice located at the second end of the inner conduit, the orifice forming part of a flow path extending from the bore, through the inner conduit, and out of the inner conduit through the orifice. Further, the lumen and slot of the support tube extend, at least in part, to a location outside the inner conduit of the compressible section when the movable element is at the second position, and said flow path further extends from the orifice, through the slot, and into the lumen at the location outside of the inner conduit.

In further more detailed aspects, the moveable element further comprises a spring section connected to the compressible section, and said flow path further extends from the orifice, and into the spring section whereby the spring section provides a portion of the internal fluid passageway. The spring section is extended when the moveable element is in the first position and when extended, the spring section has a first internal volume, and the spring section is compressed when the moveable element is in the second position and when compressed, the spring section has a second internal volume, the second internal volume of the spring section being greater than the first internal volume of the spring section whereby the internal volume of the portion of the flow path provided by the spring section is greater when the spring section is compressed.

In other features, the housing includes a narrowed region adjacent the first port, the head of the movable element being located in the narrowed region when the movable element is in the first position, the narrowed region being dimensioned so as to cause the bore of the head to close. Additionally, the housing includes a constricted region, the compressible section being located in the constricted region when the movable element is in the first position, the constricted region being dimensioned so as to cause the width of inner conduit of the compressible section to move to the first width.

Yet further, the compressible section is connected to the head, and the moveable element further comprises a spring section connected to the compressible section, the spring section being adapted to urge the movable element to the first position at which the compressible section is placed within the constricted region. In a more detailed aspect, the head, and the compressible section, and the spring section are molded as an integral moveable element.

In additional features, the compressible section comprises a plurality of relatively flexible membrane elements and a plurality of relatively stiff wall elements, the membrane elements connecting together adjacent edges of the wall elements. Further, the membrane elements are adapted to fold radially inwardly when the inner conduit has the first width.

These and other aspects and advantages of the invention will become apparent from the following detailed description and the accompanying drawings, which illustrate by way of example the features of the invention.

BRIEF DESCRIPTION OF THE DRAWINGS

FIG. 13 is a cross-sectional view of the enlarged details of FIG. 12 showing the self-expanding inner conduit at its second width, the support tube, the slot in the support tube, and showing in particular orifices existing at the base of the inner conduit that permit fluid flow from all parts of the conduit into the slot of the support tube so that there is continuous fluid flow through the entire inner conduit;

FIGS. 14 and 15 are schematic depictions of an operational principle utilized by a medical connector that incorporates aspects of the present invention.

DETAILED DESCRIPTION OF PREFERRED EMBODIMENTS

Figure 1:
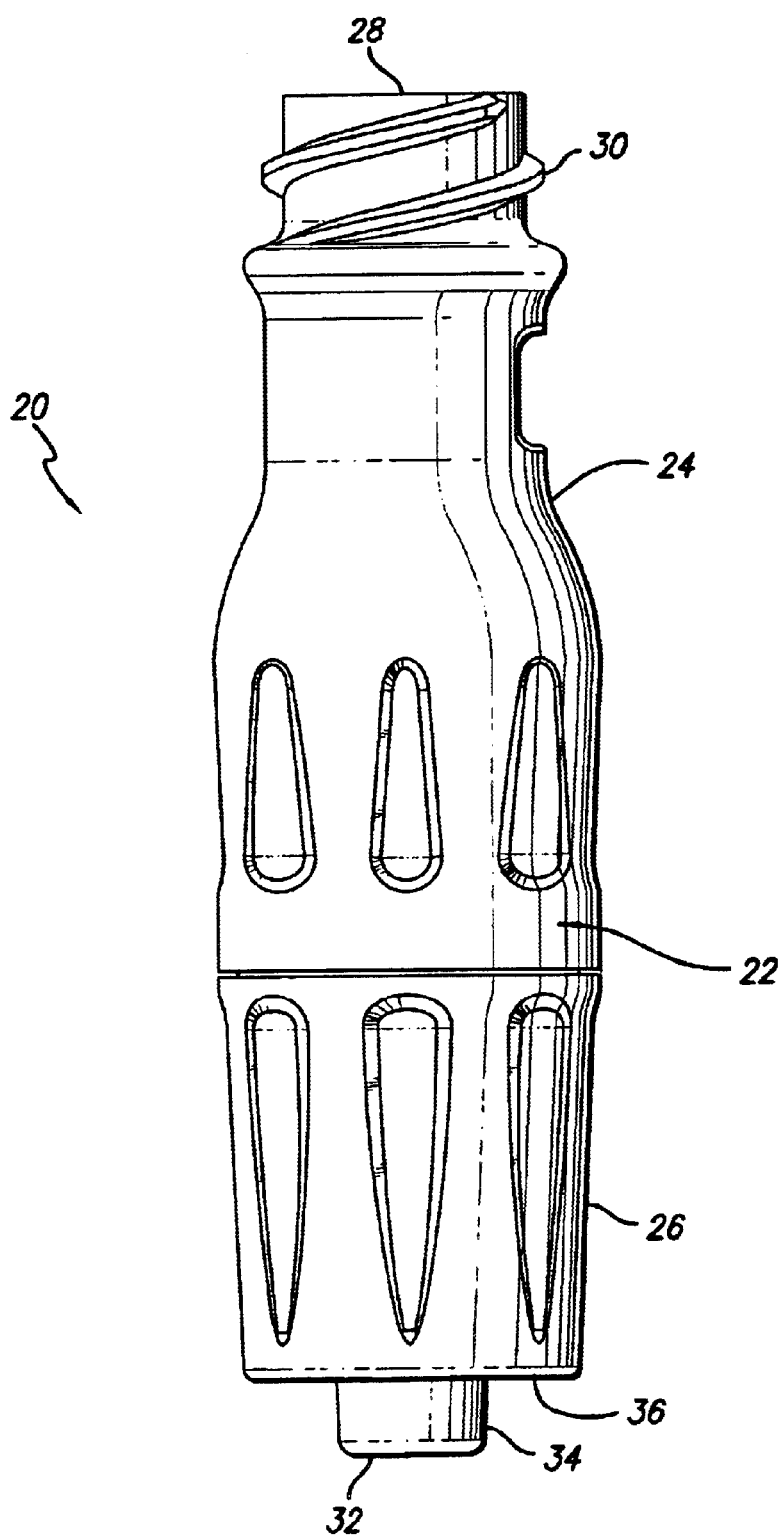
FIG. 1 is a side view of an assembled medical connector that incorporates aspects of the present invention, showing a first port surrounded by thread elements for receiving a blunt connector and a threaded cuff, and a second port comprising a blunt male connector.

Referring now in detail to the drawings in which like numerals refer to like or corresponding elements among the several figures, there is illustrated in FIG. 1 a side external view of a medical connector that includes various aspects of the present invention. The particular connector configuration exemplified in the figures is for illustration purposes only. The connector may be embodied in different configurations including, but not limited to, Y-connectors, J-loops, T-connectors, tri-connectors, PRN adapters, slip Luers, tubing engagement devices, access pins, vial adapters, blood tube adapters, bag access pins, vented adapters, and others. The drawings are for illustration purposes only.

FIG. 1 presents an embodiment of a medical connector 20 having a housing 22 that is formed of an upper housing portion 24 and a lower housing portion 26. The upper housing portion 24 has a first port 28, that in this case is a female Luer connector port with thread elements 30 located about the exterior. The lower housing portion 26 terminates in a second port 32 that, in this case, comprises a male Luer connector 34 defining a lumen 35 (lumen not visible in FIG. 1) and with a threaded locking collar 36 (threads not visible in FIG. 1). Together, the upper housing 24 and the lower housing 26 form the connector housing 22. The housing 22 may be molded of a material containing a phosphorescent colorant to render the connector 20 visible in a darkened room or may be formed of a transparent and/or opaque material.

Figure 2:
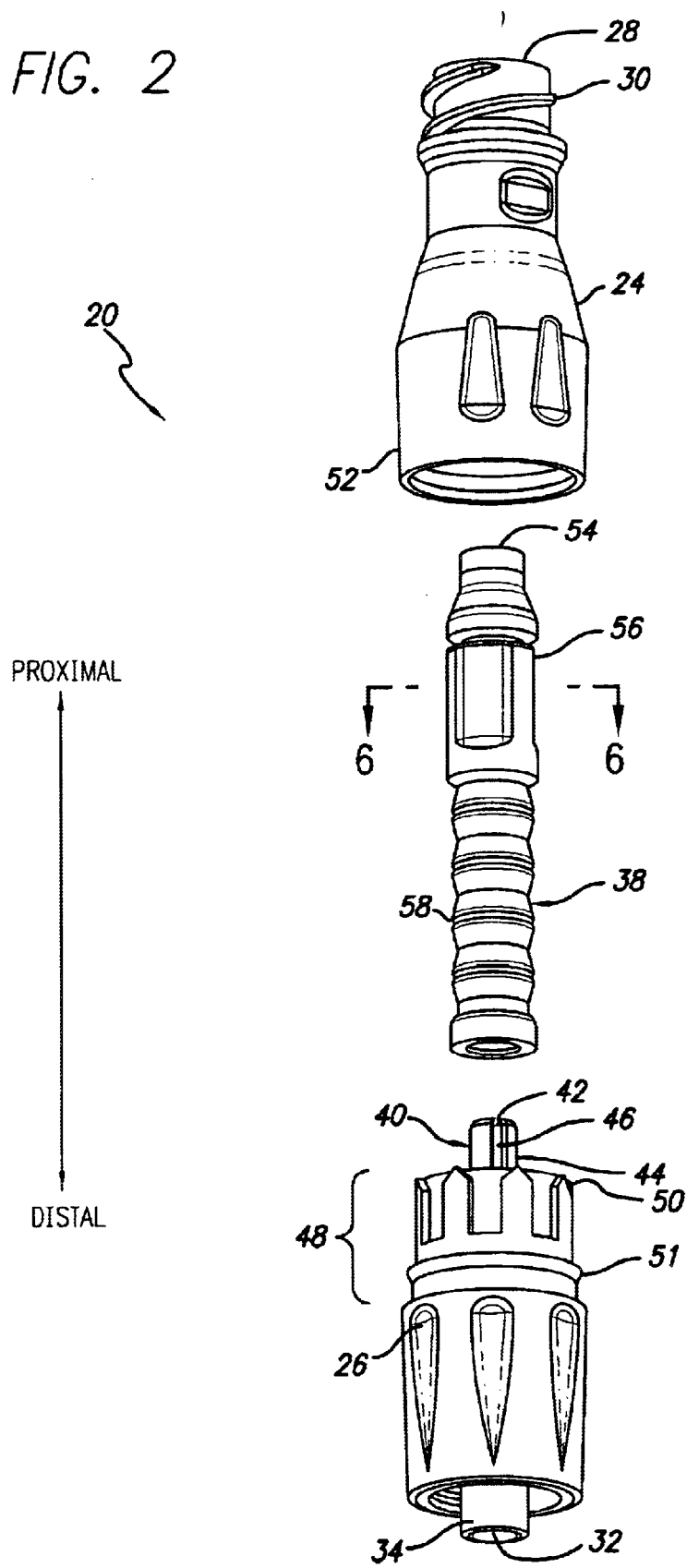
FIG. 2 is an exploded perspective view of the medical connector of FIG. 1 showing the three components of the medical connector of this embodiment, including an upper housing portion, a piston element, and a lower housing portion.

Turning now to FIG. 2, an exploded, somewhat perspective view of the connector 20 of FIG. 1 is shown. The connector 20 comprises three parts in this embodiment: the housing 22 (see FIG. 1 for numeral 22) that comprises the upper housing portion 24 and the lower housing portion 26. The connector 20 also includes a movable element or piston element 38. As will be described in more detail below, the piston element 38 is mounted over a support tube 40 that is formed as part of the lower housing portion 26. In one embodiment, the support tube 40 extends proximally from the center of the lower housing portion 26 and has an inner lumen 42 extending the length of the tube, and in the wall 44 of the tube, a longitudinal slot 46 is formed that may extend the length of the tube. In the embodiment shown, the lower housing portion 26 also includes a vent 53 used for the escape or intake of air from or to the housing during movement of the piston element 38. In another embodiment, there may not be a vent.

The housing of the embodiment shown in FIGS. 1 and 2 includes details that aid in manufacturing and that lower the costs of manufacture. As an example, the exterior surface of the upper portion 48 of the lower housing portion 26 is molded to include a crown shaped outer shell that has several crown points 50. Although not shown in FIG. 2, the interior of the lower portion 52 of the upper housing portion 24 is molded to include a complementary shaped pattern to the crown-shaped lower housing portion. The crown shapes 50 of the lower housing portion 26 mate closely with the complementary crown shapes (not shown) of the upper housing portion 24 thereby facilitating a snap-fit assembly of the medical connector housing. A snap ring 51 is also included in the lower housing portion 26 and holds the upper housing portion 24 in place on the lower housing portion 26 once the upper housing portion has been forced over the snap ring 51. The geometry of the crown shapes also prevents rotation of the upper housing portion 24 with the lower housing portion 26 when they are snapped together. Permanent assembly of the upper housing portion with the lower housing portion may also be achieved by means such as ultrasonic weld geometry, a spin weld, bonding, or by other means in other embodiments. This design has been found to result in an efficiently manufactured housing assembly that is accurately assembled, that is quickly and efficiently snapped into a secure assembly.

Figure 3:
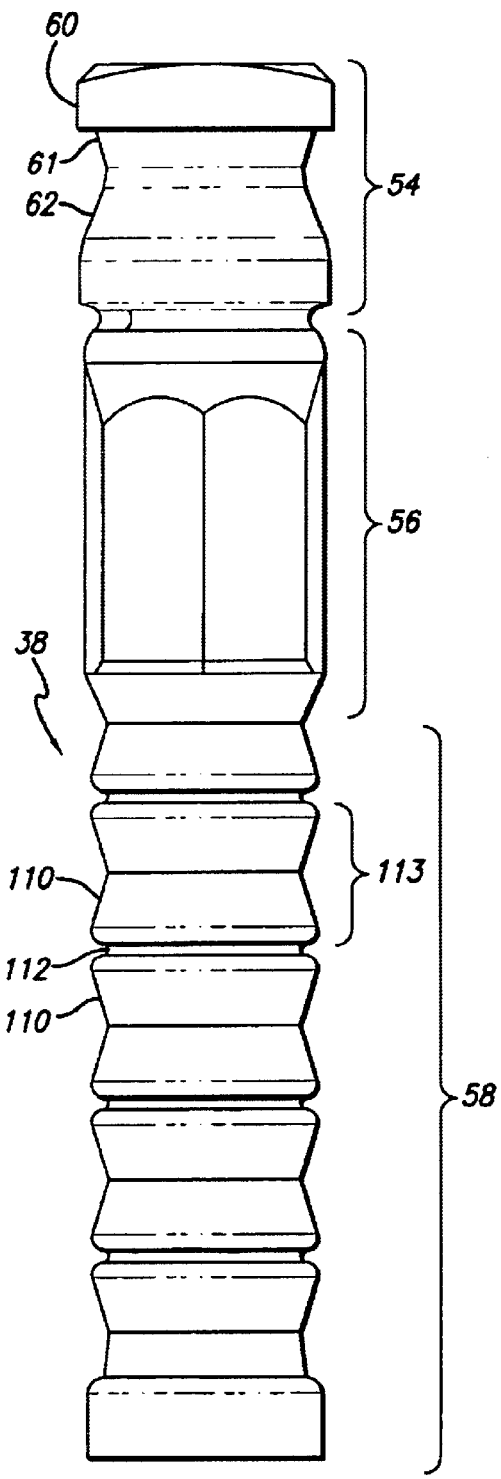
FIGS. 3 and 4 are elevational views, at right angles to each other, of the piston element shown in FIG. 2.
Figure 4:
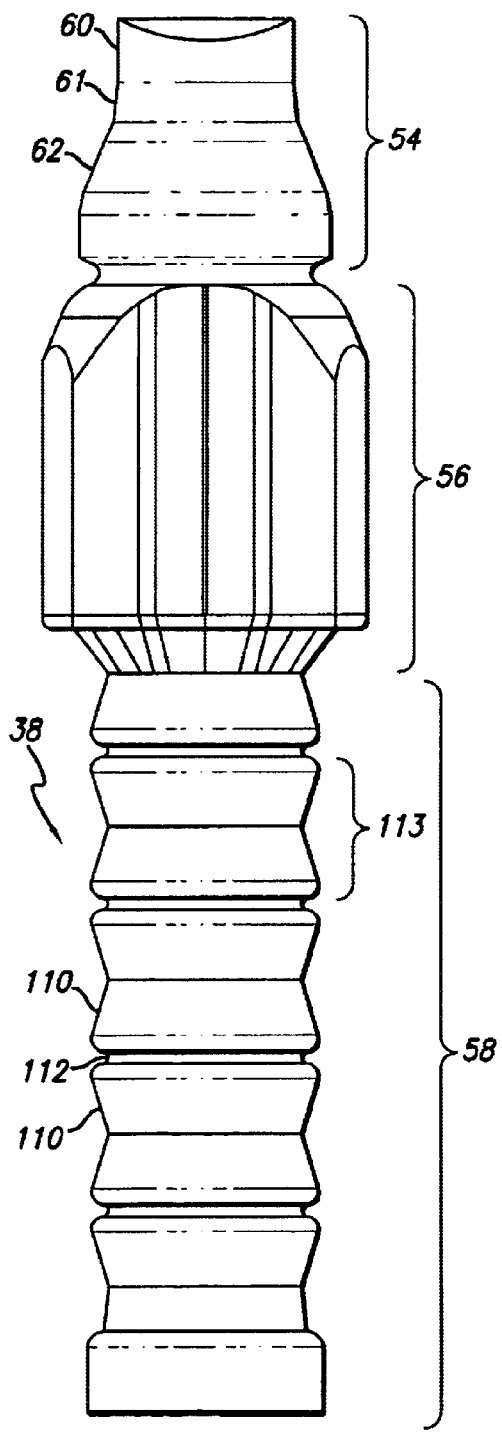

Referring now to FIGS. 3 and 4 enlarged views of a resiliently deformable piston element 38 are presented. The same piston element 38 is shown in both views, each rotated at right angles to each other. The piston element includes three main sections; a piston head 54, a compressible section 56, and a compressible section or spring section 58. The compressible section is located between the head and the spring. The piston element may suitably be molded as one piece from a resilient material such as silicone or rubber.

Figure 5:
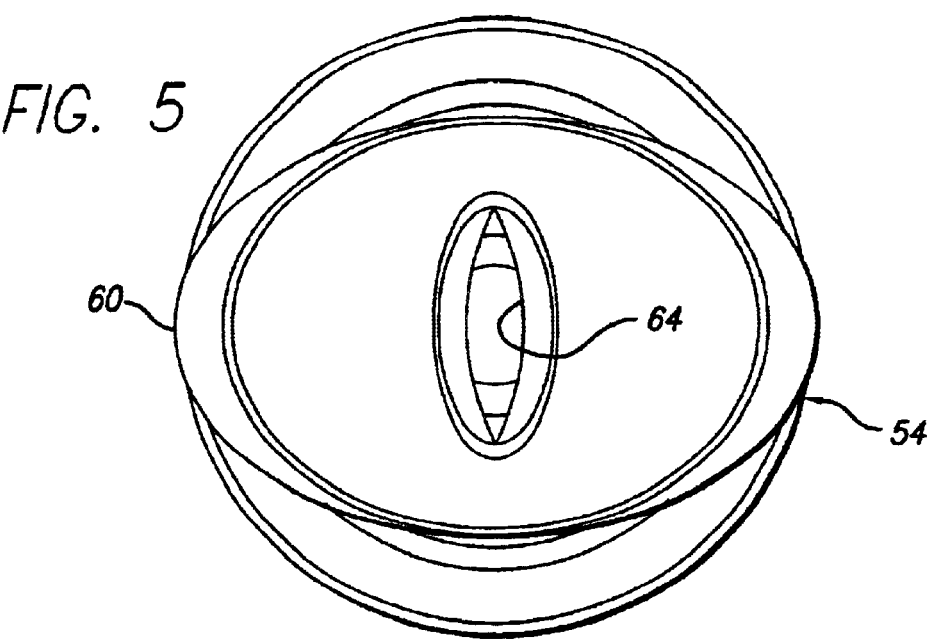
FIG. 5 is an end view of the self-opening head of the piston element of FIG. 3 showing its normally-open marquise-shaped bore and having the same orientation as the piston element of FIG. 3.

The piston head 54 includes a top portion 60 that is elliptical in outer shape, and a bottom, tapered shoulder section 62 that is circular in plan cross-section. Referring now also to FIG. 5, a marquise-shaped bore 64 is formed in the elliptically-shaped top section 60. Located between the head 54 and the shoulder section 62 is an elliptical-conical section 61 that assists in causing the marquise-shaped bore to tend to remain open. For further details on the operation of the piston head, see U.S. Pat. No. 5,676,346 to Leinsing, which is incorporated herein by reference. Although not shown in FIGS. 3, 4, or 5, the compressible section 56 includes a self-expanding inner conduit that forms one of the aspects of the invention.

Figure 6:
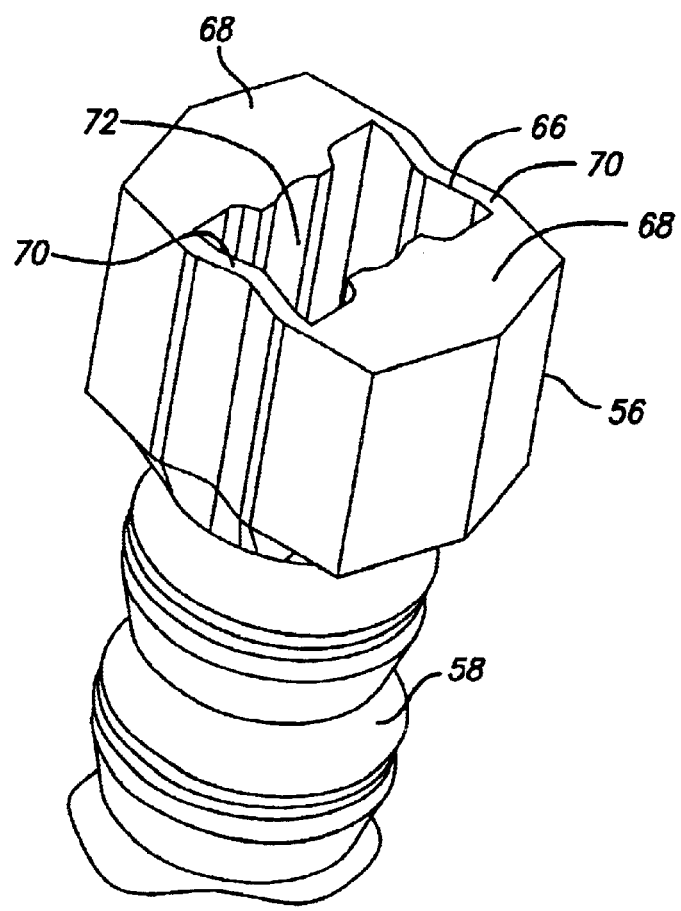
FIG. 6 is a perspective view in partial cross section of the piston element of FIG. 2 with the section taken across the line marked 6—6, showing the self-expanding inner conduit in its normally expanded condition.

Referring now to FIG. 6, a perspective cross-sectional view of the compressible section 56 is shown. As can be clearly seen, the compressible section includes an inner conduit 66 formed by two opposing relatively stiff wall elements 68 that are connected together by two opposing relatively flexible membrane elements 70. The interconnection of the wall elements 68 results in the inner conduit 66 with a width 72. It should be noted that the term "width" is not used herein in a restrictive sense; that is, it is not used to indicate the dimension in any particular direction within the inner conduit. It is used instead in a general sense to indicate the interior cross-sectional opening size of the inner conduit measured at right angles to the longitudinal axis of the moveable element.

The membrane elements 70 are adapted to fold inwardly when a radially compressive force is applied to the compressible section 56. Due to the relative stiffness of the wall elements 68, the length of the inner conduit 66 remains substantially constant under such radially compressive force. When the radially compressive force is removed or reduced, the inner conduit 66 is self-expanding and tends to expand until it is open, as shown in FIG. 6, under the force provided by the resilient material of the compressible section 56.

It can be noted that the inner conduit shown in FIG. 6 has an unusual opening shape. However, the advantageous nature of this opening shape will be apparent when later figures are discussed below.

Figure 7:
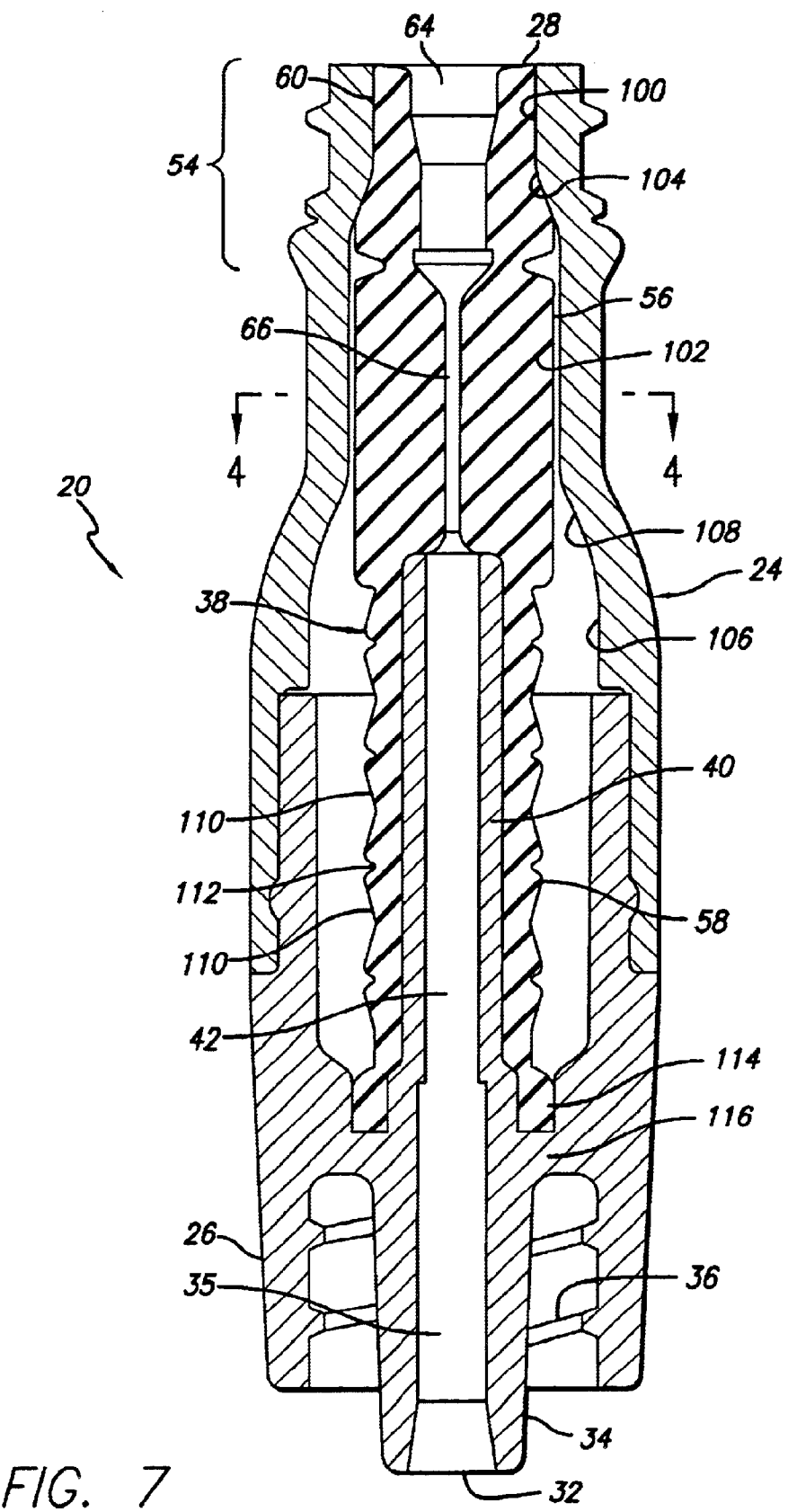
FIG. 7 is a sectional elevation of the medical connector of FIG. 1, showing the connector in a non-accessed state with the piston element in its first position in which the self-opening bore of the piston head is closed to fluid flow by the narrowed first port of the housing and the compressible section has been compressed to its first width by a narrowed region of the housing.

Referring now to FIG. 7, the connector 20 of FIG. 1 is shown in vertical cross-sectional format. It should be noted that the connector depicted in FIG. 7 is in an unaccessed state. That is, no blunt cannula has been inserted into its first port 28 for fluid communication through the connector.

The upper housing portion 24 has sections of varying internal diameter. The internal section directly adjacent the first port 28 includes a standard ANSI Luer taper portion 100 that incorporates a very slight inward taper. The center portion 102 has a larger internal diameter than the Luer taper portion 100 and is separated from the Luer taper portion 100 by a tapered lock portion 104. The bottom portion 106 of the upper housing portion 24 has a larger internal diameter than the center portion 102 and is separated from the center portion by a tapered ramp portion 108. Thus, in relation to the bottom portion 106, the center portion 102 represents a constricted region, and, in relation to the center portion 102, the Luer taper portion 100 represents a narrowed region. The bottom portion 106 has an inner diameter large enough to permit the inner conduit 66 to self-expand.

Referring now to both FIGS. 7 and 3, the spring section 58 is shown and will be discussed in more detail. In the embodiment shown, the spring section 58 is configured to include a plurality of relatively stiff annular wall portions 110 (only two of which are indicated by the numeral 110 to preserve clarity in the drawings), connected to each other by relatively flexible annular hinges 112, together forming the spring section. The annular wall portions 110 disposed at the center of the spring section have an hourglass shape 113 (see FIG. 3) that permits their bending at the center point. The hourglass shape and the hinges result in compression of the spring 58 in a controlled elastic fashion to assume a bellows-like shape in response to an axially compressive force, as will be described in relation to FIG. 10 below.

The inner diameter of the spring section 58 is selected to allow positioning of the spring over the support tube 42 and the outer diameter of the spring is selected to allow positioning of the spring within the housing 22. The spring is easily slidable over the support tube 42 in the embodiment shown but when a compressive force is applied to the spring, the support tube prevents the spring from buckling and assists the spring in a controlled change to a bellows-type shape.

Figure 9:
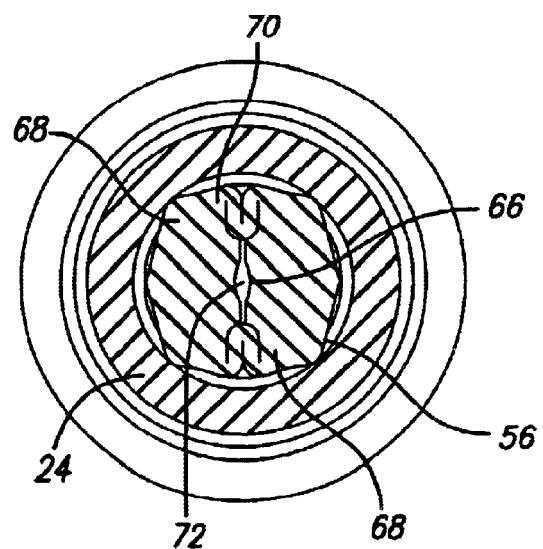
FIG. 9 is a sectional view of the medical connector of FIG. 7, taken across the line marked 9—9 showing the compressible section in its compressed configuration.

In the unaccessed state of the connector 20 as shown in FIG. 7, the spring section 58 of the piston element 38 urges the compressible section 56 through the ramp portion 108 of the upper housing portion 24 into the relatively constricted center portion 102. The location of the compressible section 56 in this constricted location causes compression of the compressible section and the inner conduit, as shown in FIG. 9. A radially compressive force is applied to the compressible section that causes the membrane elements 70 to fold inwardly and the stiff wall elements 68 to move toward each other as shown in FIG. 9, thereby substantially reducing the width 72 of the inner conduit 66 to a first compressed width, that is much less than the second expanded width of the inner conduit 66 shown in FIG. 6. Had there been any fluid in the inner conduit 66 when it had its second width, as shown in FIG. 6, most, if not all, of that fluid would be expelled as the inner conduit assumed the first width shown in FIG. 9.

The cross-sectional view of FIG. 7 shows the interaction of the three parts of the connector of the embodiment discussed. The upper housing portion 24 includes the first port 28 that comprises a female Luer connector port with thread elements 30 located about the exterior, and is securely connected to the lower housing portion 26. The lower housing portion 26 includes the second port 32 that comprises the male Luer connector 34 with a threaded locking collar 36. The internal threads are visible in FIG. 7. The lower housing portion 26 also includes the support tube 40 integrally formed with the lower housing portion. In this embodiment, the support tube has a length that results in its location somewhat within the first housing portion 24 when the complete housing has been assembled. This feature is also apparent from FIG. 2.

Figure 8:
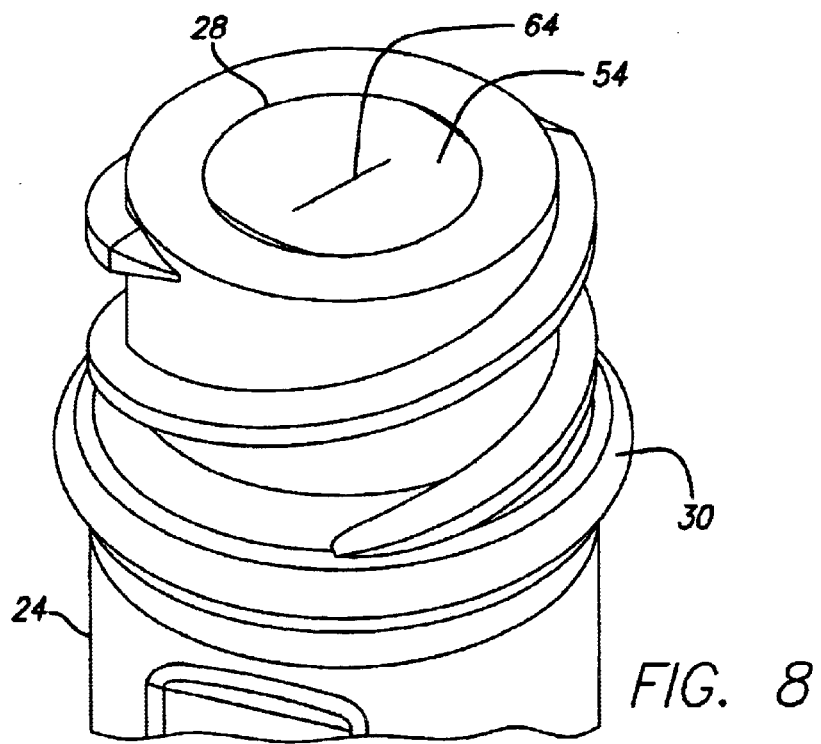
FIG. 8 is an enlarged perspective view of the first port of the connector of FIG. 1 showing the self-opening head of the piston element in the first position with the marquise shaped bore closed to fluid flow.

Further, the movable element or piston 38 is shown mounted over the support tube and extending to the first port 28 of the upper housing portion 24. The piston head 54 is within the narrowed Luer taper region 100 of the first housing portion and this narrowing has caused a compressive force to be exerted against the elliptical portion 60 of the piston head 54, thereby causing the marquise-shaped bore 64 to be closed. This closed configuration is more clearly shown in FIG. 8 where the top of the piston head can be seen and the closed bore 64 is clearly seen. It should also be noted that this configuration permits easy wiping of the piston head before use. This closed bore 64 blocks the fluid flow through the valve in this unaccessed state.

It should be noted that the fluid volume within the connector 20 in this unaccessed state is defined by the open portion in the piston head under the closed bore 64, the inner conduit 66 through the compressible section, the lumen 42 of the support tube and the second port 32. It is also informative to note that the support tube and second port are rigid structures and their internal volumes do not change with the connector being accessed, as will be discussed below. While the bore 64 of the piston head may appear to be open in FIG. 7, it is closed. The particular orientation of the cross section in FIG. 7 results in the marquise-shaped bore being shown along its length, and thus has the appearance of being open. However, a perspective view of the top of the piston head, such as that shown in FIG. 8, demonstrates that the bore is closed.

In further reference to FIG. 7, the spring includes a base 114 that is mounted at the base 116 of the support tube 40. The spring may be held in place at the base of the support tube by friction, adhesive, or other means. For example, in the present embodiment, the movable element 38 is placed in the lower housing portion 26 with the spring section 58 over the support tube 40 and the base 114 positioned as shown, and the upper housing portion 24 is placed over the movable element 38 and secured to the lower housing portion as described above. Because the dimensions of the upper housing portion and the lower housing portion are such that there is constant, although limited, axial compressive pressure placed on the movable element 38, the spring section 58 tends to stay in position as shown. This may be referred to as a pre-load force. Incorporated U.S. Pat. No. 5,676,346 to Leinsing may be referred to for further details. Extending proximally from the center of the base 116 is the support tube 40. Extending distally from the base is the male-Luer taper connector 34 having a lumen 35 that is coaxial with the lumen 42 of the support tube 40.

Figure 10:
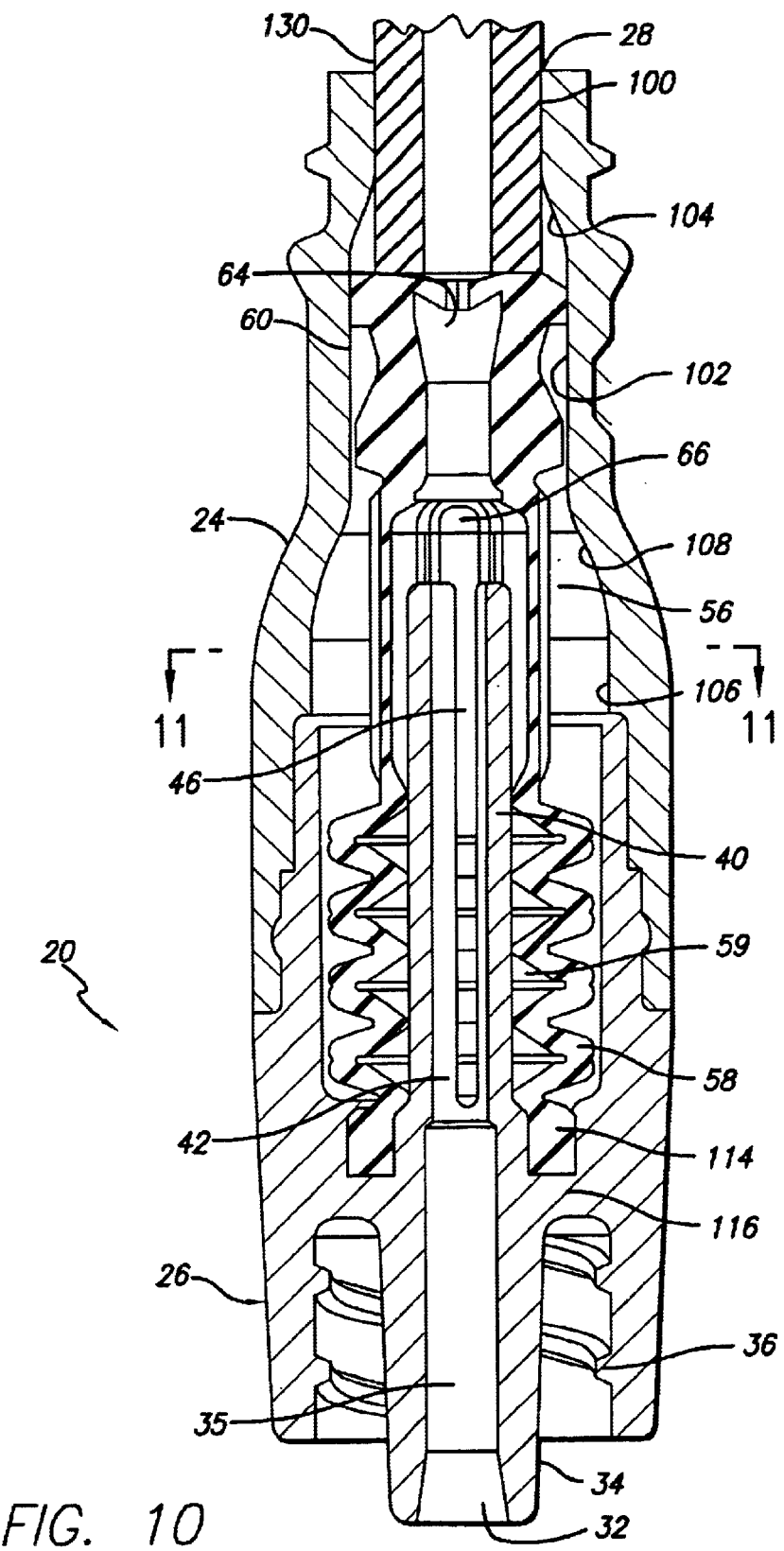
FIG. 10 is a sectional elevation of the medical connector of FIG. 1, showing the connector in an accessed state with the piston element having been moved to its second position in which the self-opening bore of the piston head has opened to fluid flow and the self-expanding conduit of the compressible section has expanded to its normal "as-molded" state, or second width, for increased internal volume.

Turning now to FIG. 10, the connector 20 in an accessed state is shown. A blunt cannula 130, which is a male Luer connector in this case, has been inserted into the first port 28 into contact with the top section 60 of the piston element head and has moved the piston element so that the compressible section 56 is now partially over the support tube 40. The spring 58 is now compressed.

As is described in U.S. Pat. No. 5,676,346 to Leinsing, the configuration of the piston head results in the bore 64 of the piston head being self-opening. That is, the bore 64 is normally open and radial compressive forces must be applied to the piston head to close the bore. The elliptical-conical portion 61 (see FIGS. 3 and 4) of the piston element head 54 also uses the axial force from insertion of the male Luer 130 to facilitate the opening of the bore 64. Thus, when the male cannula 130 presses the piston head into the larger interior of the housing 22 and radial compressive forces are removed from the piston head, the bore 64 self-opens to now permit fluid flow through the connector 20.

Similarly, the compressible section 56 is configured so that the inner conduit 66 is self-expanding. That is, the inner conduit 66 is normally at its second width and radial compressive forces must be applied to the compressible section to close the inner conduit, or to force it to have its smaller first width. Thus, when the male cannula 130 presses the piston head into the larger interior of the housing 22, and radial compressive forces are removed from the compressible section, the inner conduit 66 self-expands to its larger second width that will now permit a larger fluid volume within the fluid passageway of the connector 20. This larger width either exactly compensates for the decrease in length of the fluid passageway through the connector or adds additional volume to the fluid passageway. As can be seen by reference to FIG. 10, pressing the male cannula 130 into the connector 20 shortens the length of the fluid passageway through the connector from the length in FIG. 7 and would otherwise thereby reduce the volume of the fluid flow path also. However, the increased width of the inner conduit volumetrically counteracts this decrease in length. This is discussed in more detail below in regard to FIGS. 14 and 15.

Figure 12:
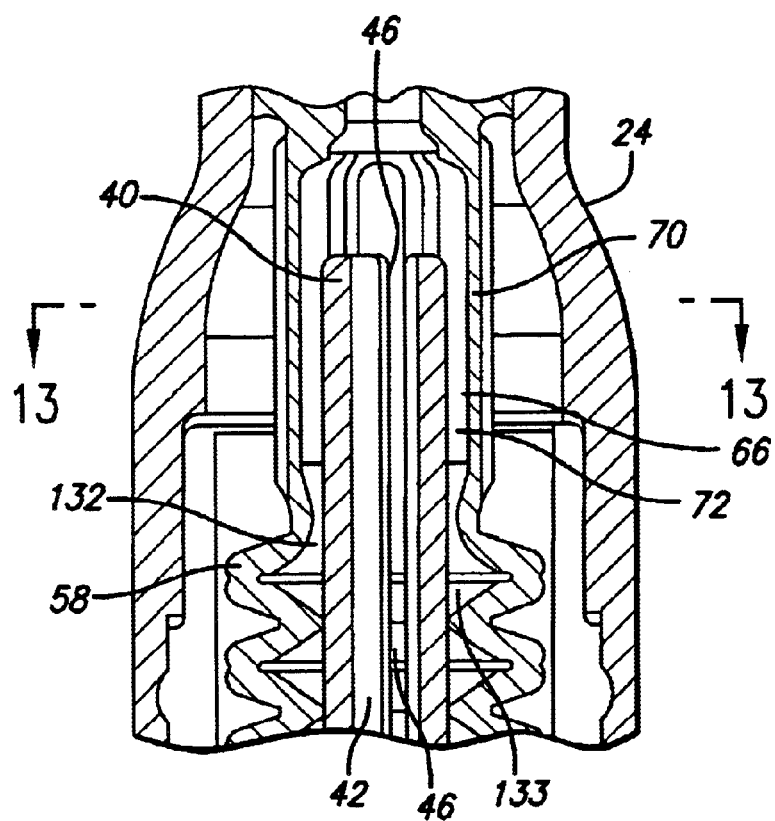
FIG. 12 is a detail view of the portion of FIG. 10 showing in enlarged detail the interaction of the slot and lumen in the support tube with the self-expanded inner conduit of the compressible section, and the action of the spring section on the compressible section.

In FIG. 10, it is shown that the compressible section 56 and the inner conduit 66 are now located partially over the support tube 40. This arrangement can be seen in greater detail in the enlarged diagram of FIG. 12. The support tube however includes a lumen 42 through which fluid may flow and a longitudinal slot 46 in the wall 44 of the tube through which fluid may continuously flow into and out of the support tube lumen and into and out of the inner conduit as shown in FIG. 10. Fluid that may reach the spring section will also flow into or out of the slot of the support tube so that continuous flow occurs throughout the connector when in the accessed state. No reservoirs or dead space of any nature exist so that each part of the fluid passageway is adapted for continuous flow through it.

Figure 11:
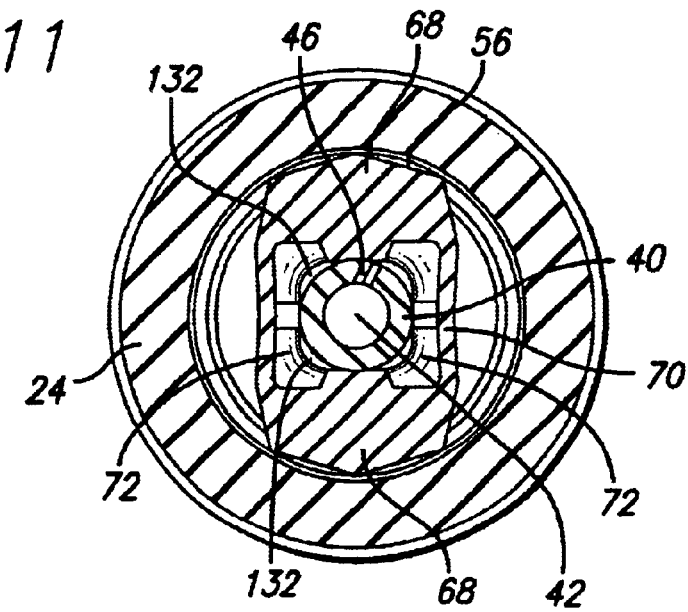
FIG. 11 is a sectional view of the medical connector of FIG. 7 taken across line 11—11 showing the self-expanding conduit of the compressible section at its normal "as-molded" state, or second width for increased internal volume.

Turning now also to FIG. 11 in conjunction with FIG. 10, the interaction of the support tube 40, its lumen 42, and its slot 46 with the inner conduit 66 may be seen from another angle. FIG. 11 is a cross sectional view of FIG. 10, which is a connector in the accessed state. In FIG. 11, a possible orientation of the slot of the support tube with the inner conduit wall is shown. In this configuration, the slot 46 of the support tube resides against one of the stiff walls 68 of the inner conduit. This particular positioning does not prevent fluid flow through the inner conduit because orifices 132 are provided at the bottom of the inner conduit to provide for fluid flow between the inner conduit and the proximal portion of the spring section. The enlarged diagram in FIG. 13 shows the orifices 132 more clearly. In the accessed state, the point of connection between the spring section 58 and the compressible section 56 may be configured to define the orifices 132 through which the support tube 40 protrudes. Thus, at the distal end of the inner conduit 66, a plurality of gaps or orifices 132 may be defined between the piston element 38 and the support tube 40 which collectively provide a fluid flow path between all portions of the inner conduit 66 and the proximal section 133 (see FIG. 12) of the spring section 58, from whence fluid may flow into the lumen 42 of the support tube via the slot 46.

Thus, the compressible section 56 is configured so that when the connector 20 is accessed by a blunt cannula 130, fluid may flow continuously through the entire inner conduit 66 without a reservoir being developed at any point in which fluid may be trapped, held, or retained. The piston element 38 is configured to provide a larger fluid passageway width at the location of the compressible section 56 when the connector is in the accessed state, as shown in FIG. 10, thus increasing the volume of the fluid passageway or keeping it the same as the volume of the fluid passageway in the unaccessed state, as shown in FIG. 7.

It will be appreciated that, when the slot 46 of the support tube is oriented so that it is facing one of the membrane elements 70 in FIG. 11, fluid may flow directly between the lumen 42 of the tube and the inner conduit 66 via the slot 46 or in parallel with fluid flow through the orifices 132.

To briefly reiterate, in the accessed state as shown in FIG. 10, the internal fluid passageway through the connector 20 is through the bore of the piston element, through the head of the piston element, through the entire inner conduit 66, through the lumen 42 of the support tube, and through the second port 32. It will be appreciated that flow may be reversed when fluid is withdrawn through the connector. It should be noted that in comparison to FIG. 7, the internal fluid passageway of FIG. 10 has been shortened by the amount that the blunt cannula 130 has entered the first port 28, or, put another way, the amount by which the inner conduit 66 now covers the support tube 40. However, the self-expansion of the inner conduit to a greater width has volumetrically compensated for the decrease in length of the internal fluid passageway. Conversely, as the blunt male connector 130 is withdrawn from the first port 28, the internal fluid passageway through the connector will lengthen, but at the same time the width of the inner conduit will decrease. If the decrease in width decreases the volume of fluid in the internal fluid passageway of the connector by an amount greater than the increase in length causes an increase in volume, a bolus of fluid may be expelled by the connector 20 through the second port.

In further detail, the inner conduit will be discussed. Referring to FIGS. 9 and 11, the membrane elements 70 may be adapted to fold inwardly when a radially compressive force is applied to the compressible section. Due to the relative stiffness of the wall elements 68, the length 134 of the inner conduit 66 remains substantially constant under such radially compressive force. Where the radially compressive force is removed or reduced, the inner conduit 66 is self-expanding and tends to expand under the force provided by the resilient material of the compressible section 56.

In regard to the spring section 58, the piston element 38 resiliently deforms so as to permit the annular portions 110 to alternatingly deform inwardly and outwardly, while allowing rotation to occur mainly at the hinges 112, as exemplified in FIG. 10. A comparison of the two spring section 58 configurations shown in FIGS. 7 and 10 will reveal that when in the configuration of FIG. 10, the spring section 58 also contributes to the increased internal fluid passageway through the connector resulting from insertion of the male Luer into the connector. Because the longitudinal slot 46 extends substantially along the entire spring section length in the configuration of FIG. 10, fluid may continuously flow within the spaces 59 formed between the spring section and the support tube 40 resulting from the action of the hinges 112 during compression of the spring section.

Referring to FIG. 7, the spring section 58 is in an extended configuration when the moveable element 38 is in the first position; i.e., the connector 20 has not been accessed by a male Luer. As can be seen, the spring section is located quite close to the support tube 40 along its entire length. At this location, the spring section has a first internal volume. When the connector 20 has been accessed and the moveable element 38 has been located at its second position as shown in FIG. 10, the spring section 58 has been compressed. In compression, parts of the spring section remain close to the support tube 40 while other parts move outwards forming the spaces 59 indicated in FIG. 10. Taking the internal volume of the spring section, which includes the parts near and the parts farther away from the support tube 40, the spring section has a second internal volume, and that second internal volume is greater than the first internal volume (extended, or uncompressed, spring section). Because of this configuration and the fact that the slot in the support tube extends into the spring section, the spring section forms a part of the internal fluid passageway through the connector. In the embodiment shown, the spring section contributes to a net volume increase of that internal fluid passageway when the connector is accessed. Conversely, when the connector is unaccessed; i.e., when the male Luer 130 is being withdrawn, the spring section will collapse to the configuration shown in FIG. 7 thereby contributing to a decrease in the net volume of the internal fluid passageway through the connector.

Figure 16:
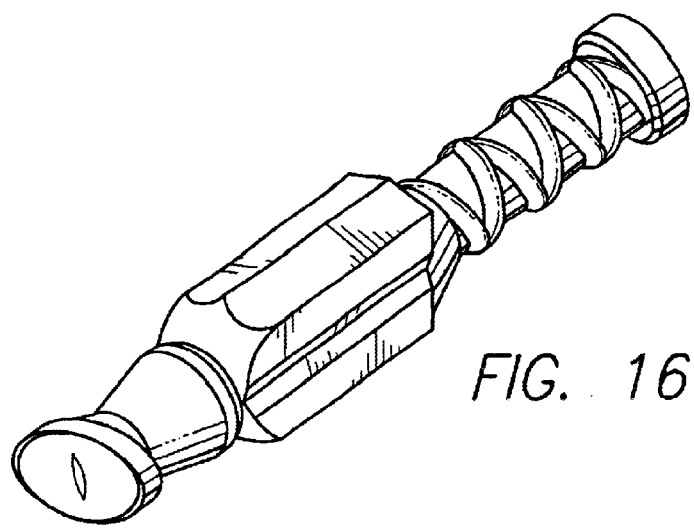
FIGS. 16 through 18 are perspective views of the piston element showing alternative configurations of the spring section.
Figure 17:
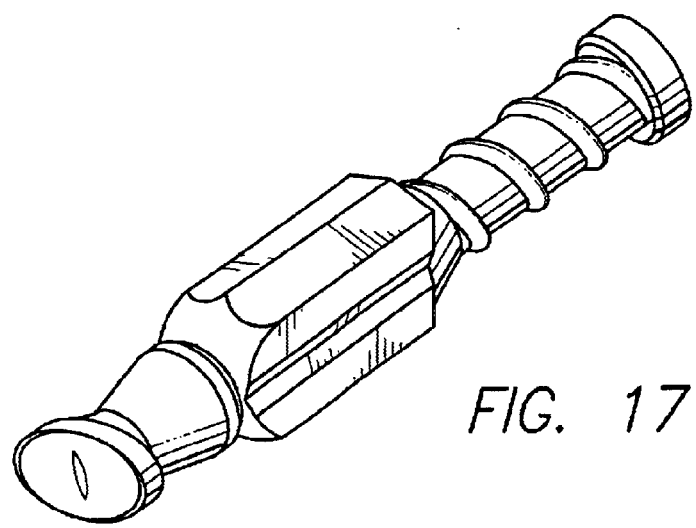
Figure 18:
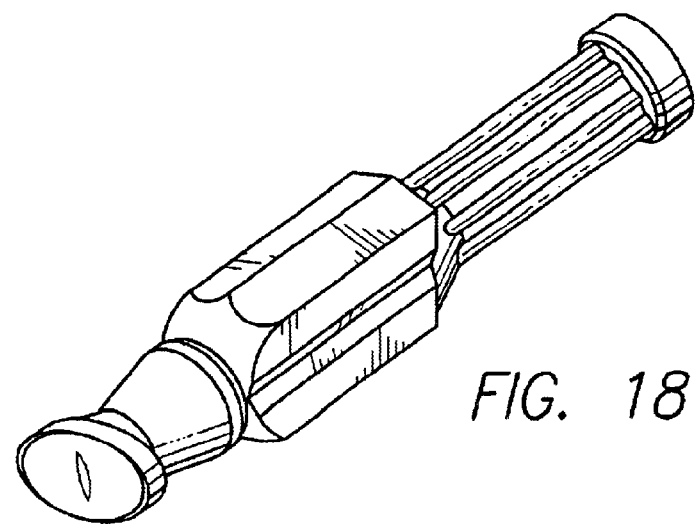

It will be appreciated that modifications in the shapes of the spring section are possible. Changes may be made to affect flow rate, restoring force, spring section return rate, volume, differential volume between compression and extension configurations, sealing, piston retention, and acceptance of blunt cannulas. Modifications include changing the number of annular sections, wall thickness and height, or may include different configurations of the spring section entirely, as exemplified in FIGS. 16–18.

The use of the support tube 40 also has another advantage. Because it takes up volume in the internal fluid passageway by virtue of its size, there is less volume for fluid in that passageway when the connector is not accessed (shown in FIG. 7). This results in a smaller fluid passageway in the unaccessed state than might otherwise exist if no support tube were present. Because it is rigid, it has a fixed volume that will not change.

FIGS. 14 and 15 are schematic drawings that present the concept of the adjustment of the volume of the internal fluid passageway through a connector based on expansion and contraction of a part of that passageway. In FIG. 14, a schematic connector 136 is shown that includes an internal fluid passageway 138 having a length 140 linking a first port 142 with a second port 144. In FIG. 14, the single dashed line adjacent the first sport 142 is used to indicate the closed bore of the piston head. Forming part of the fluid passageway 138 is an inner conduit 146 having a first width 148. In FIG. 15, a blunt cannula 150 has been inserted into the first port 142 of the connector 136 and has shortened the internal fluid passageway 138 which now has a length shown by numeral 154. The difference between the length 140 of the internal fluid passageway in FIG. 14 and the length 154 of the internal fluid passageway in FIG. 15 is shown by numeral 156. If nothing else were to change, the volume of the internal fluid passageway 138 of FIG. 15 would now be less than that of FIG. 14, and a negative bolus effect could be expected upon removal of the male cannula 150. However, the width 160 of the inner conduit 146 in FIG. 15 has been expanded to be greater than the width 148 of the inner conduit of FIG. 14. It will be appreciated that, by appropriate selection of the expanded and compressed widths of the inner conduit, the volume of the fluid path 138 can be made to increase, stay the same, or decrease when a blunt cannula is made to access the connector 136. Where the volume increases, a positive bolus-effect is created when the cannula is removed from the connector. Where the volume remains the same, a neutral-bolus effect is created, and, where the volume decreases, a negative-bolus effect is created.

Turning now to the operation of the medical connector 20, the connector is initially in its unaccessed state or closed position as shown in FIG. 7. The resiliency of the spring section 58 of the piston element 38 causes the piston head 54 to be biased into the narrowed ANSI Luer taper portion 100.

The shoulder 62 of the piston head 54 contacts the tapered lock portion 104 of the upper housing portion 24 and controls the position of the top of the piston head 54 in relation to the edge of the first port 28 thus forming a swabable surface therewith. The sharp pointed ends of the marquise-shaped bore 64 facilitate a tight seal upon compression of the bore along its minor axis and by compression of the top section 60 of the piston head 54 along its major axis.

Just prior to accessing the connector with a male Luer connector at the first port 28, the top surface of the piston head 54 and the edge of the first port may be cleaned by, for example, passing a sterilizing swab over the smooth surface of the piston head lying flush, slightly below, or slightly above the upper surface of the first port. The connector is then ready to be accessed by a standard male Luer connector with or without a threaded locking collar.

The tip of a male Luer connector is brought into contact with the proximal surface of the top section 60 of the piston head 54. The application of sufficient pressure causes the spring section 58 of the piston element 38 to axially contract and to compress in a bellows-like configuration so that orifices 132 are defined between the spring section 58 and the support tube 40. As the spring section 58 axially contracts, the piston head 54 moves out of the narrowed ANSI Luer taper portion 100 of the upper housing portion 24 and into the center portion 102. As the piston head 54 clears the tapered lock portion 104 and is moved into the center portion 102, the larger internal diameter of the center portion allows the top section 60 of the piston head to self-expand and to tend to assume its normal elliptical shape and the same action allows the bore 64 to tend to self-open to assume its normally open marquise-shape bore configuration thereby opening a fluid passageway through the connector and the piston head 54.

Further, as the spring section 58 contracts under axial pressure of the male Luer tip 130, the compressible section 56 moves in the distal direction from the constricted center portion 102 of the upper housing 24 into the larger diameter bottom portion 106 of the upper housing, allowing the compressible section to self-expand and to assume an expanded configuration. As the compressible section 56 moves in the distal direction, the support tube 40 will extend into the inner conduit 66.

As the blunt cannula 130 becomes fully inserted in the connector 20, the compressible section fully self-expands, thereby expanding the width of the inner conduit 66. Flow may now occur through the connector. The internal fluid passageway through the connector has expanded in width to volumetrically compensate for the decrease in length, and fluid flows continuously through every part of the internal fluid passageway of the connector. Additionally, fluid flows through the entire compressible section 56 due to the slot 46 in the wall 44 of the support tube 40 and the orifices 132 that permit fluid flow through the distal end of the inner conduit 66 into the proximal section 133 of the spring section and into the slot 46.

When the blunt cannula 130 is withdrawn from the connector 20 to allow the connector to return to the non-accessed state, the restoring force generated by the spring section 58 of the piston element 38 causes the compressible section 56 to be urged proximally past the ramp section 108 into the constricted confines of the center section 102 of the upper housing portion 24 and thus into the compressed condition where the inner width 72 of the inner conduit decreases to its first width, as shown in FIG. 7. Thus, the volume of the fluid passageway through the conduit may decrease, depending on the selected dimensions of the compressible section 56 and its inner conduit 66. If so, a bolus of fluid that was within the inner conduit will be expelled through the second port 32. Simultaneously, the elliptical top portion 60 of the piston head 54 is guided by the tapered lock section 104 into the ANSI Luer taper section 100 where it is once again urged into a narrowed circular shape to close off the orifice 64 and reestablish a positive seal against fluid flow through the connector 20.

Thus there has been shown and described a new and useful valve for use in medical connectors that provides a controllable bolus effect. Depending on the expanded and compressed widths selected for the inner conduit 66 of the compressible section in relation to the configuration of the balance of the piston element 38, a positive-bolus, neutral-bolus, or negative-bolus effect can be achieved as the connector is placed in an unaccessed state from an accessed state.

It will be apparent from the foregoing that while particular embodiments of the invention have been illustrated and described, various modifications can be made without departing from the spirit and scope of the invention. Accordingly, it is not intended that the invention be limited, except as by the appended claims.

What is claimed is:

1. A connector for controlling the flow of fluid, the connector having an internal fluid passageway by which fluid may flow through the connector, the connector comprising:

a housing having a first port and a second port, the first port being adapted to receive a blunt cannula and the second port adapted for fluid communication with a fluid conduit; and a movable element positioned within the housing, the movable element having a first position at which the movable element blocks fluid flow through the housing and a second position at which the movable element permits fluid flow through the housing, the movable element comprising:

a head defining a bore forming a part of the fluid passageway through the connector, the head being configured such that when the movable element is in the second position, the bore self-opens to permit fluid flow, the head being further configured such that when the moveable element is in the first position the bore moves to a closed configuration preventing fluid flow;

a compressible section defining an inner conduit forming a part of the fluid passageway through the connector, the inner conduit having a width moveable between a first width and a second width, the compressible section being configured so that when the moveable element is in the second position the compressible section self-expands so that the inner conduit has the second width, the inner conduit being further configured so that when the moveable element is in the first position the inner conduit moves to the first width, wherein the first width is smaller than the second width;

a support tube having opposing ends, the support tube defining a lumen extending between the opposing ends, one end being in fluid communication with the second port and the lumen forming a part of the internal fluid passageway through the connector;

wherein the support tube comprises a wall, the wall defining a slot providing a fluid path between the exterior of the tube and the lumen.

2. The connector of claim 1, wherein the support tube is configured in relation to the moveable element such that, when the movable element is in the second position, the lumen and slot of the support tube are positioned, at least in part, within the inner conduit of the compressible section such that fluid may flow through the inner conduit of the compressible section, through the slot, through the lumen of the support tube, and through the second port of the housing.

3. The connector of claim 2 wherein:
the inner conduit of the compressible section has opposing first and second ends, the first end being adjacent the bore of the head; and
the movable element defines an orifice located at the second end of the inner conduit, the orifice forming part of a flow path extending from the bore, through the inner conduit, and out of the inner conduit through the orifice.

4. The connector of claim 3 wherein:
the lumen and slot of the support tube extend, at least in part, to a location outside the inner conduit of the compressible section when the movable element is at the second position; and
said flow path further extends from the orifice, through the slot, and into the lumen at the location outside of the inner conduit.

5. The connector of claim 3 wherein:
the moveable element further comprises a spring section connected to the compressible section; and
said flow path further extends from the orifice, and into the spring section whereby the spring section provides a portion of the internal fluid passageway.

6. The connector of claim 5 wherein:
the spring section is extended when the moveable element is in the first position and when extended, the spring section has a first internal volume; and
the spring section is compressed when the moveable element is in the second position and when compressed, the spring section has a second internal volume, the second internal volume of the spring section being greater than the first internal volume of the spring section;
whereby the internal volume of the portion of the flow path provided by the spring section is greater when the spring section is compressed.

7. A connector for controlling the flow of fluid, the connector having an internal fluid passageway by which fluid may flow through the connector, the connector comprising:
a housing having a first port and a second port, the first port being adapted to receive a blunt cannula and the second port adapted for fluid communication with a fluid conduit; and
a movable element positioned within the housing, the movable element having a first position at which the movable element blocks fluid flow through the housing and a second position at which the movable element permits fluid flow through the housing, the movable element comprising:
a head defining a bore forming a part of the fluid passageway through the connector, the head being configured such that when the movable element is in the second position, the bore self-opens to permit fluid flow, the head being further configured such that when the moveable element is in the first position the bore moves to a closed configuration preventing fluid flow;
a compressible section defining an inner conduit forming a part of the fluid passageway through the connector, the inner conduit having a width moveable between a first width and a second width, the compressible section being configured so that when the moveable element is in the second position the compressible section self-expands so that the inner conduit has the second width, the inner conduit being further configured so that when the moveable element is in the first position the inner conduit moves to the first width, wherein the first width is smaller than the second width; and wherein the inner conduit is configured such that fluid may continuously flow through the entire inner conduit when the movable element is in the second position; and
a support tube having opposing ends, the support tube defining a lumen extending between the opposing ends, one end being in fluid communication with the second port and the lumen forming a part of the internal fluid passageway through the connector;
wherein the support tube comprises a wall, the wall defining a slot providing a fluid path between the exterior of the tube and the lumen.

8. The connector of claim 7 wherein the support tube is configured in relation to the moveable element such that, when the movable element is in the second position, the lumen and slot of the support tube are positioned, at least in part, within the inner conduit of the compressible section such that fluid may flow through the inner conduit of the compressible section, through the slot, through the lumen of the support tube, and through the second port of the housing.

9. The connector of claim 8 wherein:
the inner conduit of the compressible section has opposing first and second ends, the first end being adjacent the bore of the head; and
the movable element defines an orifice located at the second end of the inner conduit, the orifice forming part of a flow path extending from the bore, through the inner conduit, and out of the inner conduit through the orifice.

10. The connector of claim 9 wherein:
the lumen and slot of the support tube extend, at least in part, to a location outside the inner conduit of the compressible section when the movable element is at the second position; and
said flow path further extends from the orifice, through the slot, and into the lumen at the location outside of the inner conduit.

11. The connector of claim 10 wherein:
the moveable element further comprises a spring section connected to the compressible section; and
said flow path further extends from the orifice, and into the spring section whereby the spring section provides a portion of the internal fluid passageway.

12. The connector of claim 11 wherein:
the spring section is extended when the moveable element is in the first position and when extended, the spring section has a first internal volume; and
the spring section is compressed when the moveable element is in the second position and when compressed, the spring section has a second internal volume, the second internal volume of the spring section being greater than the first internal volume of the spring section;
whereby the internal volume of the portion of the flow path provided by the spring section is greater when the spring section is compressed.

13. A connector for controlling the flow of fluid, the connector having an internal fluid passageway by which fluid may flow through the connector, the connector comprising:
a housing having a first port and a second port, the first port being adapted to receive a blunt cannula and the second port adapted for fluid communication with a fluid conduit;

a movable element positioned within the housing, the movable element having a first position at which the movable element blocks fluid flow through the housing and a second position at which the movable element permits fluid flow through the housing, the movable element comprising:

a head defining a bore forming a part of the fluid passageway through the connector, the head being configured such that when the movable element is in the second position, the bore self-opens to permit fluid flow, the head being further configured such that when the moveable element is in the first position the bore moves to a closed configuration preventing fluid flow;

a compressible section defining an inner conduit forming a part of the fluid passageway through the connector, the inner conduit having a width moveable between a first width and a second width, the compressible section being configured so that when the moveable element is in the second position the compressible section self-expands so that the inner conduit has the second width, the inner conduit being further configured so that when the moveable element is in the first position the inner conduit moves to the first width, wherein the first width is smaller than the second width, the inner conduit being configured such that fluid may continuously flow through the entire inner conduit when the movable element is located in the second position; and a support tube having a first end and a second end with the second end being in fluid communication with the second port, the support tube having a lumen forming a part of the internal fluid passageway through the connector, the support tube having a wall that defines the lumen and a longitudinal slot formed through the wall and into communication with the lumen whereby fluid may flow into and out of the lumen through the longitudinal slot;

wherein the lumen and slot of the support tube are located within the inner conduit of the compressible section when the movable element is in the second position whereby fluid may flow through the inner conduit of the compressible section, through the slot, through the lumen of the support tube, and through the second port of the housing.

14. The connector of claim 13 wherein:

the inner conduit of the compressible section has a first end and a second end; and the movable element also comprises an orifice located at the second end of the inner conduit that provides a flow path between the inner conduit and a location of the fluid passageway that is outside of the inner conduit.

15. The connector of claim 14 wherein:

the lumen and slot of the support tube extend to a location outside the inner conduit of the compressible section when the movable element is at the second position; and the orifice provides a flow path between the inner conduit and the slot and the lumen of the support tube at the location outside of the inner conduit.

16. The connector of claim 15 wherein:

the moveable element further comprises a spring section connected to the compressible section, the spring section located over the lumen and slot of the support tube that extend to the location outside the inner conduit; and the orifice provides the flow path through the spring section.

17. The connector of claim 16 wherein:

the spring section is extended when the moveable element is in the first position and when extended, the spring section has a first internal volume; and the spring section is compressed when the moveable element is in the second position and when compressed, the spring section has a second internal volume, the second internal volume of the spring section being greater than the first internal volume of the spring section;

whereby the internal volume of the portion of the flow path provided by the spring section is greater when the spring section is compressed.

18. The connector of claim 13 further comprising a narrowed region adjacent the first port of the housing at which the head of the movable element is located when the movable element is in the first position, the size of the narrowed region selected so as to cause the bore of the head to close to prevent fluid flow through the fluid passageway of the connector.

19. The connector of claim 13 further comprising a narrowed region adjacent the first port of the housing at which the compressible section is located when the movable element is in the first position, the size of the narrowed region selected o as to cause the inner conduit of the compressible section to move to its second width.

20. The connector of claim 19 wherein:

the compressible section is connected to the head; and the moveable element further comprises a spring section connected to the compressible section, the spring section being adapted to urge the movable element to the first position at which the compressible section is placed within the narrowed region.

21. The connector of claim 20 wherein the head, and the compressible section, and the spring section are molded as an integral element from a resilient material.

22. The connector of claim 13 wherein the compressible section comprises a plurality of substantially inflexible wall elements and a plurality of substantially flexible membrane elements, the membrane elements connecting together adjacent edges of the wall elements.

23. The connector of claim 22 wherein the membrane elements are adapted to fold radially inwardly when the inner conduit has the second width.

* * * * *

UNITED STATES PATENT AND TRADEMARK OFFICE
CERTIFICATE OF CORRECTION

PATENT NO. : 6,802,490 B2
DATED : October 12, 2004
INVENTOR(S) : Karl R. Leinsing and Theodore J. Mosler It is certified that error appears in the above-identified patent and that said Letters Patent is hereby corrected as shown below:

Column 18,
Line 36, delete "o" and insert -- so --.

Signed and Sealed this

Thirty-first Day of May, 2005

JON W. DUDAS
*Director of the United States Patent and Trademark Office*